United States Patent
Pallaro (10) Patent No.: US 7,365,303 B2
(45) Date of Patent: Apr. 29, 2008

(54) OPTICAL SENSOR DEVICE TO BE INSTALLED ON BOARD A MOTOR-VEHICLE FOR AID IN DRIVING AND/OR FOR AUTOMATIC ACTIVATION OF SYSTEMS PROVIDED ON THE MOTOR-VEHICLE

(75) Inventor: Nereo Pallaro, Orbassano (IT)

(73) Assignee: C.R.F. Società Consortile per Azioni, Orbassano (Turin) (IT)

(*) Notice: Subject to any disclaimer, the term of this patent is extended or adjusted under 35 U.S.C. 154(b) by 67 days.

(21) Appl. No.: 11/522,342

(22) Filed: Sep. 18, 2006

(65) Prior Publication Data
US 2007/0090311 A1 Apr. 26, 2007

(30) Foreign Application Priority Data
Oct. 21, 2005 (EP) .................................. 05425745

(51) Int. Cl.
*G01N 15/06* (2006.01)
(52) U.S. Cl. ................. 250/221; 348/148; 250/227.25; 250/575
(58) Field of Classification Search ................ 250/573, 250/574, 575, 221, 208.1, 227.25; 348/148; 340/602
See application file for complete search history.

(56) References Cited

U.S. PATENT DOCUMENTS 6,130,421 A * 10/2000 Bechtel et al. ........... 250/208.1
2004/0141057 A1* 7/2004 Pallaro et al. ............. 348/148

FOREIGN PATENT DOCUMENTS

| DE | 197 55 008 A1 | 7/1999 |
| EP | 1 418 089 A2 | 5/2004 |
| EP | 1 418 089 B1 | 5/2006 |
| WO | WO 99/15381 | 4/1999 |

* cited by examiner

Primary Examiner—Que Tan Le
Assistant Examiner—Stephen Yam
(74) Attorney, Agent, or Firm—Nixon & Vanderhye P.C.

(57) ABSTRACT

An optical sensor device that can be installed on board a motor vehicle for aid to driving and/or for automatic activation of one or more on-board systems according to the environmental conditions detected comprises a sensor module including an array of the CCD or CMOS type, the sensitive area of which is split into sub-areas dedicated to different functions, which are separate from one another and set at a distance apart, and located adjacent to the four vertices of the sensitive area of the array.

11 Claims, 10 Drawing Sheets

OPTICAL SENSOR DEVICE TO BE INSTALLED ON BOARD A MOTOR-VEHICLE FOR AID IN DRIVING AND/OR FOR AUTOMATIC ACTIVATION OF SYSTEMS PROVIDED ON THE MOTOR-VEHICLE

BACKGROUND OF THE INVENTION

The present invention relates to an optical sensor device that can be installed on board a motor vehicle and that can be used as an aid to driving and/or for automatic activation of on-board systems of the motor vehicle.

In particular, the invention regards an optical sensor device of the type comprising:

- an optical sensor in the form of a CCD or CMOS array, having a sensitive area in which a number of sub-areas is defined, each of which is designed for a specific optical function corresponding to monitoring of the scene in front of the motor vehicle and/or to detection of environmental parameters; and
- a plurality of optical systems with different directions of the optical axis and/or fields of vision, designed to send optical signals to respective sub-areas of the sensitive area of said array, for the purpose of performing the aforesaid functions, in which at least some of said sub-areas are defined by different and separate portions of the sensitive area of said array dedicated to different optical functions, and in which said different and separate portions of the sensitive area of the array include at least:

- a first portion of the top part of the sensitive area, defining a first sub-area, for detection of fog in front of the motor vehicle;
- a second and different portion of the sensitive area, defining a second sub-area, for detection of a twilight condition;
- a bottom portion of the sensitive area, defining a third sub-area, separate from said first and said second sub-areas, for monitoring the scene in front of the motor vehicle;
- a further portion of the top part of the sensitive area, defining a fourth sub-area different and separate from the first, second and third sub-areas, for detecting the presence of raindrops or of mist on the windscreen or on the rear window of the motor vehicle;
- a first optical system for conveying optical signals on said first sub-area for detection of fog, including a light emitter for emitting light in the direction of the space in front of the motor vehicle, a receiver for receiving light scattered by the fog possibly present in front of the motor vehicle, and optical means for directing the light received only on said first sub-area of the sensitive area of said array; and
- a second optical system, a third optical system, and a fourth optical system, provided for directing optical signals on said second, third and fourth sub-areas of the sensitive area of said array, respectively for detection of a twilight condition, for monitoring of the scene in front of the motor vehicle, with particular reference to a condition in which the vehicle crosses another vehicle coming in the opposite direction or to a condition of passing through a tunnel, and for detection of raindrops or of mist on the window of the motor vehicle.

A sensor device having all the aforesaid characteristics has formed the subject of the European patent application No. EP 1 418 089 A2, filed in the name of the present applicant.

SUMMARY OF THE INVENTION

The purpose of the present invention is to improve further the device previously proposed, in particular for the purpose of:

- increasing the level of "integration", i.e., enabling, given the same sensitive area of the array, a greater number of integrated functions, or, given the same function, a reduction of the sensitive area and hence of the array;
- reducing the dimensions of the optical system and hence of the overall dimensions of the sensor device;
- controlling better the position and orientation of the optical elements with respect to one another and with respect to the sensitive area of the array;
- controlling better the separation between sub-areas of the sensitive area of the array; and
- simplifying the process of fabrication and assembly of the sensor device.

With a view to achieving the above and further purposes, the subject of the present invention is a sensor device having the characteristics specified in the annexed claim 1.

Further preferred and advantageous characteristics of the invention are indicated in the dependent claims.

BRIEF DESCRIPTION OF THE DRAWINGS

The invention will now be described with reference to the annexed plate of drawings, provided purely by way of non-limiting example, in which.

DETAILED DESCRIPTION OF THE INVENTION

Figure 1:
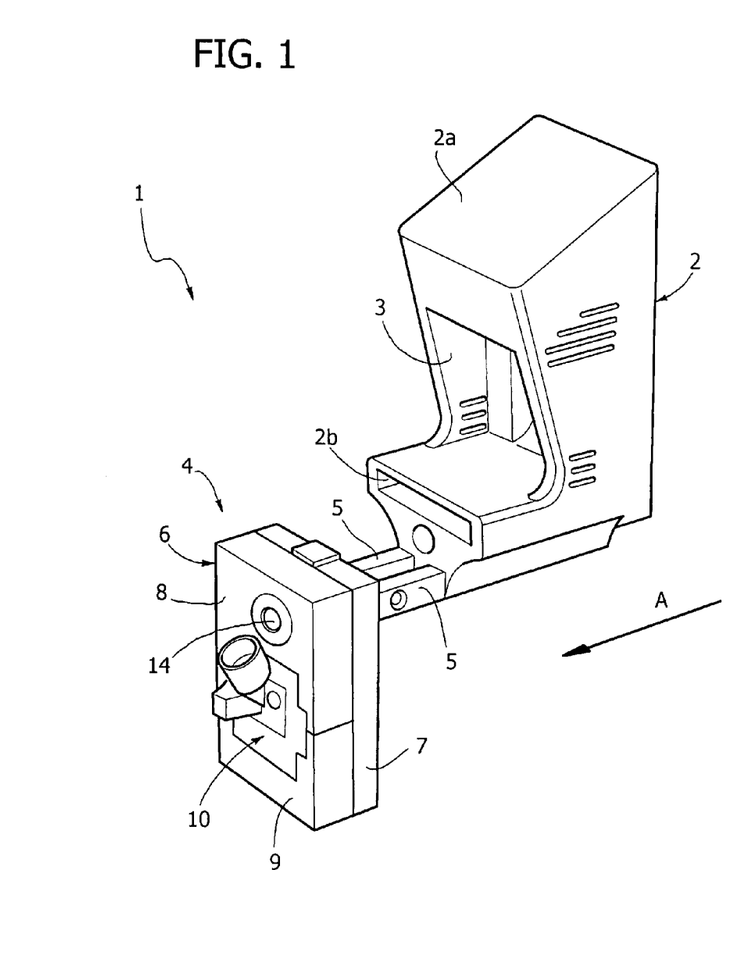
FIG. 1 is a perspective view of an example of embodiment of the sensor device according to the invention, together with the corresponding supporting system.

FIG. 1 illustrates an example of embodiment of the sensor device according to the invention designed to be applied adjacent to the internal surface of the windscreen of a motor vehicle so as to enable optical monitoring of the scene in front of the vehicle. The device according to the invention can, however, be installed also in other areas of the motor vehicle, for example adjacent to the internal surface of the rear window, to enable monitoring of the scene behind the vehicle. In the case of the example illustrated, the sensor device, which is designated as a whole by the reference number 1, includes a supporting structure 2 that is constituted by the usual support of the internal rear-view mirror of the motor vehicle, modified accordingly. The support 2 has a top surface 2*a* designed to adhere to the internal surface of the windscreen and has a body having a cavity 3 open towards the front, i.e., in the direction of advance of the motor vehicle, which is indicated by the arrow A in FIG. 1 (see also FIGS. 3 and 4). The aforesaid cavity is designed to receive the lighting devices of any known type (not illustrated), designed to illuminate the surface of the windscreen in order to enable detection of the presence of raindrops or of mist on the windscreen by an optical receiver of the reflected light radiation, as will be illustrated in detail in what follows.

Figure 3:
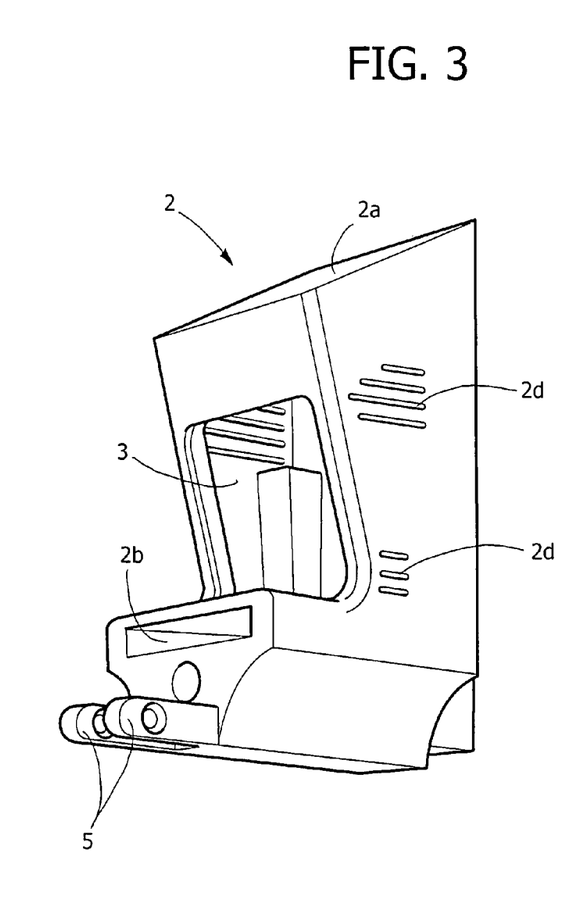
FIGS. 3 and 4 are two perspective views of a detail of the support illustrated in FIG. 1.
Figure 4:
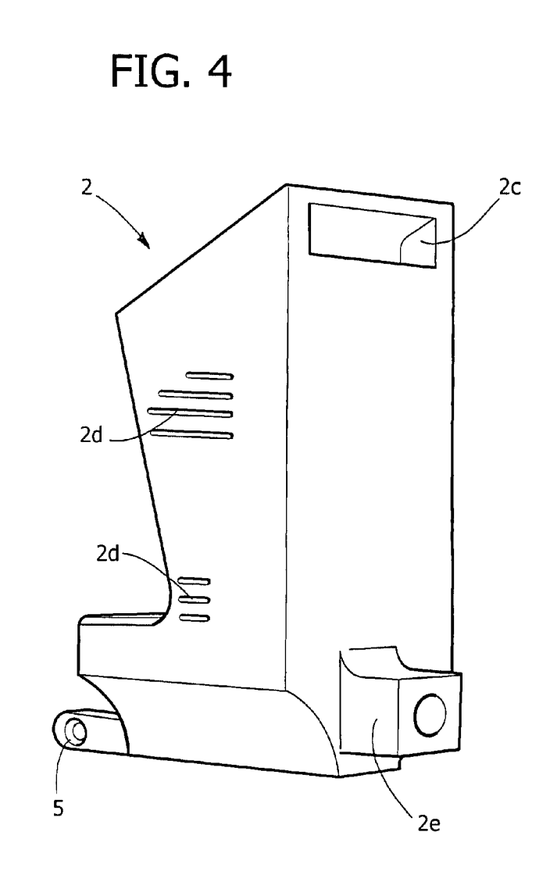

The cavity 3 is also traversed by a flat cable for electrical connection of the optical sensor provided on a sensor unit 4 connected in a detachable way on attachment arms 5 projecting at the front from the bottom end of the body of the support 2 (see also FIG. 3). The body of the support 2 also has a passage 2*b* in a position corresponding to its bottom end, which gives out at the front, and a passage 2*c* (FIG. 4) at its top end, which gives out at the back. The passages 2*b*, 2*c* enable outlet of the flat cable that traverses the body 2, respectively, in the direction of the sensor unit 4 and of the electrical circuit on board the motor vehicle. With reference again to FIGS. 1, 3 and 4, the cavity 3 is delimited laterally by walls having slits 2*d* for aeration of the lighting devices provided within the cavity 3. Finally, FIG. 4 shows an appendage 2*e* projecting at the back from the bottom end of the support 2, designed to enable fixing of the internal rear-view mirror of the motor vehicle, according to a technique in itself known.

Figure 2:
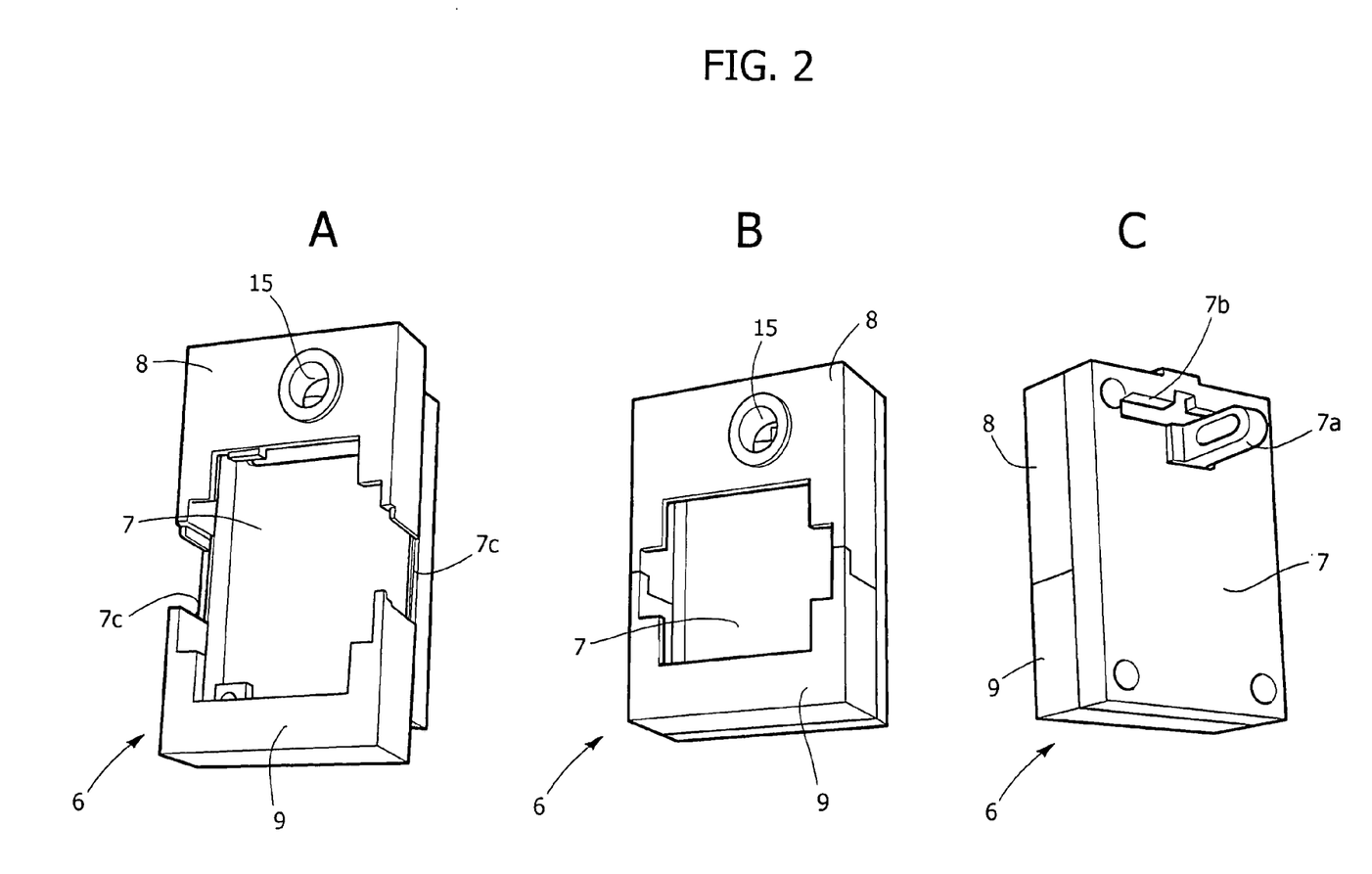
FIG. 2 comprises three perspective views of a support-container of the sensor device, used in the example of embodiment of FIG. 1.

With reference to FIG. 2, in the case of the specific example illustrated, the sensor unit 4 has an auxiliary supporting structure, designated as a whole by 6 in FIGS. 2A, B, C. The auxiliary supporting structure 6 comprises a rear plate 7 provided with an appendage 7*a* for connection to the attachment 5 of the support 2, as well as an outlet 7*b* for passage of the flat cable that is guided through the support 2.

Figure 5:
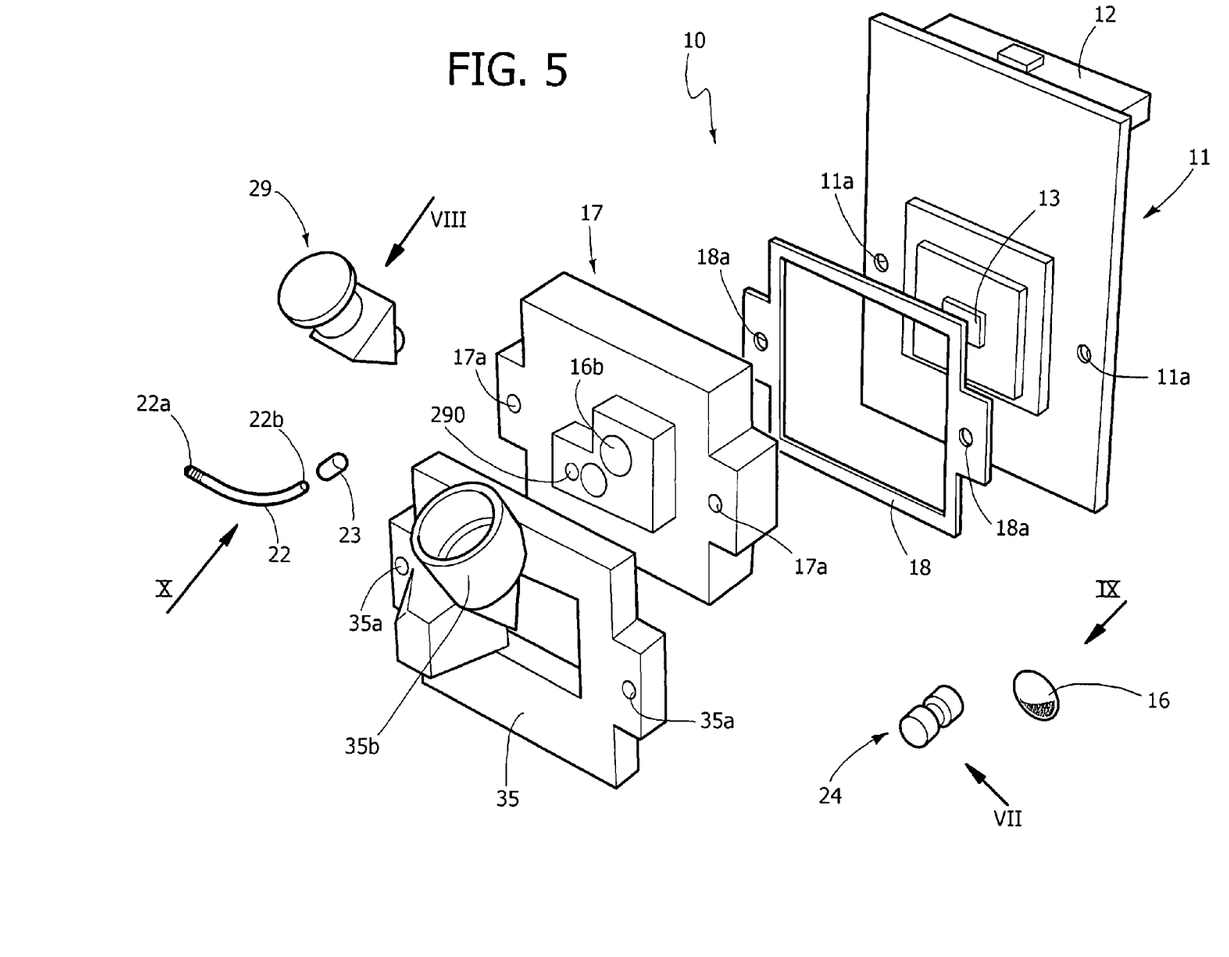
FIG. 5 is an exploded perspective view of the main components of the sensor device according to the invention.

The rear plate 7 has, on its front surface, a pair of parallel vertical rails 7*c*, set at a distance from one another (FIG. 2A), on which are slidably mounted, between a position where they are at a distance from one another (FIG. 2A) and a position where they are close to one another (FIG. 2B), a pair of supports 8, 9, designed to grip between them a sensor module 10. FIG. 1 illustrates the sensor module in the condition where it is mounted between the two supports 8, 9 set alongside one another. FIG. 5 shows an exploded perspective view of the sensor module 10.

With reference to FIG. 5, the sensor module 10 has a rear plate, constituted by a printed-circuit board (PCB) 11 provided at the back with connectors 12 for connection to one or more flat conductors, and bearing at the front an optical sensor 13, constituted by an array of optical sensors of the CCD or CMOS type.

Figure 11:
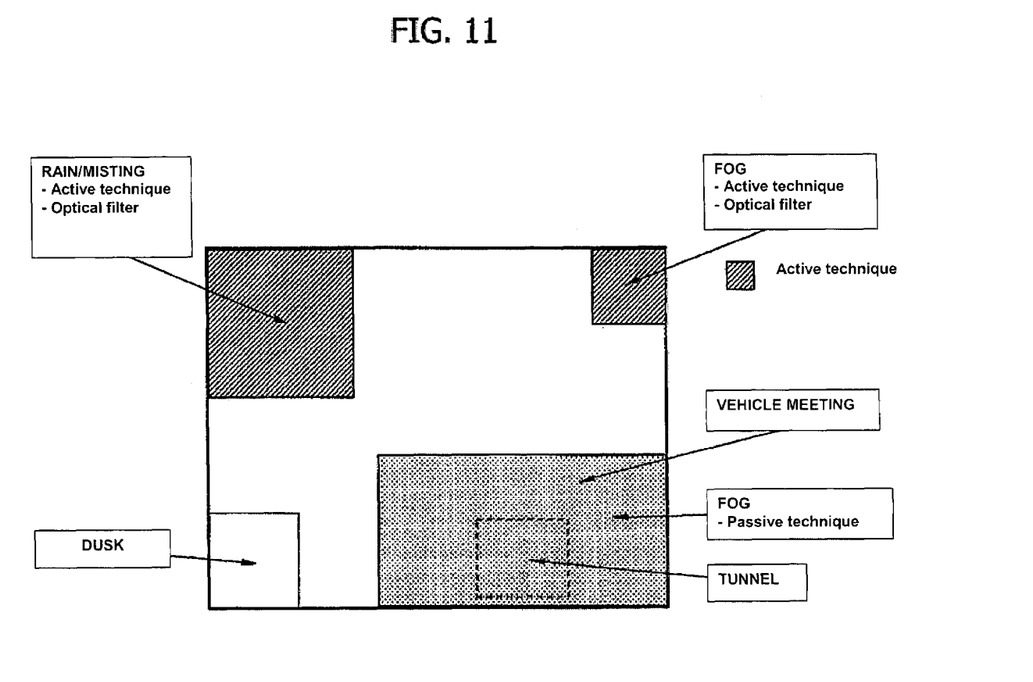
FIG. 11 is a schematic front view of the sensitive area of the array of optical sensors used in the device according to the invention, which shows a preferred division of said sensitive area into sub-areas dedicated to specific functions.

FIG. 11 of the annexed plate of drawings is a schematic illustration of the sensitive area of the sensor array 13 and shows how said area is split into sub-areas dedicated to different specific functions. As will be described in detail in what follows, in fact, the sensor device is provided with a plurality of optical systems, each of which is designed to perform a specific optical function from among a series of possible functions, such as monitoring of the scene in front of the vehicle, with particular reference to the crossing of another oncoming vehicle, or to passing through a tunnel, or the detection of a twilight condition, or the detection of presence of raindrops or of mist on the windscreen, or the detection of fog in front of the motor vehicle, and so forth. Each of said optical systems is prearranged, as will be seen, in such a way as to receive the optical signals at input thereto in a specific one of the aforesaid sub-areas so as to enable the system to carry out simultaneously all the aforesaid specific functions. In this way, the system is able to provide a useful aid to the driver in driving the motor vehicle and/or to activate automatically one or more on-board systems of the motor vehicle, according to the environmental conditions detected.

As may be seen in FIG. 11, a portion of the top part of the sensitive area of the array 13, adjacent to the top right vertex (as viewed in the example illustrated in FIG. 11) of said area, is dedicated to detection of fog via an active technique, i.e., through detection of the light radiation scattered by the fog following upon lighting by a light emitter dedicated for said purpose.

In the case of the example illustrated, the light emitter that enables detection with an active technique of the fog is constituted by a LED source 14 (FIG. 1) housed in a seat 15 (FIG. 2) made on the front surface of the support 8.

Figure 6:
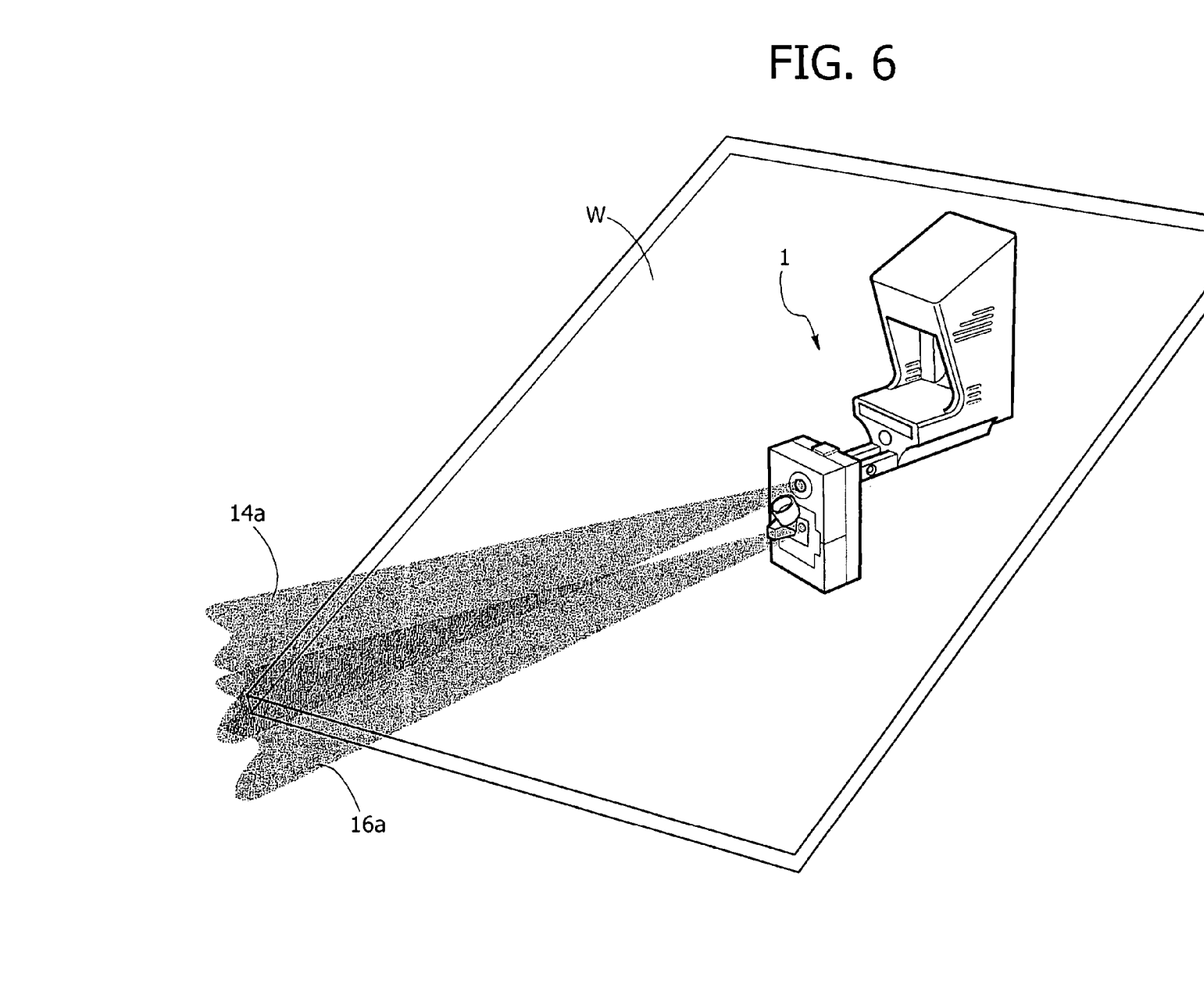
FIG. 6 is a schematic perspective view that shows the working principle of the optical system with emission and reception of back-scattering radiation used for detection of fog, or, in general, said visibility in the environment surrounding the vehicle.

FIG. 6 is a schematic illustration of the sensor device 1 in the position of installation on the internal surface of a windscreen W and shows the cone 14*a* of lighting of the LED 14. The same figure also shows the cone 16*a* constituting the field of vision of the receiver of the light radiation that is scattered by any fog that may be present in front of the motor vehicle, the receiver comprising a lens 16 (FIG. 5) that is designed to be mounted in a seat 16*b* of a plate support 17, which is screwed to the plate 11, with the interposition of a frame 18, via screws that engage holes 17*a*, 18*a* and 11*a* made respectively in the supports 17, 18 and 11.

Figure 9:
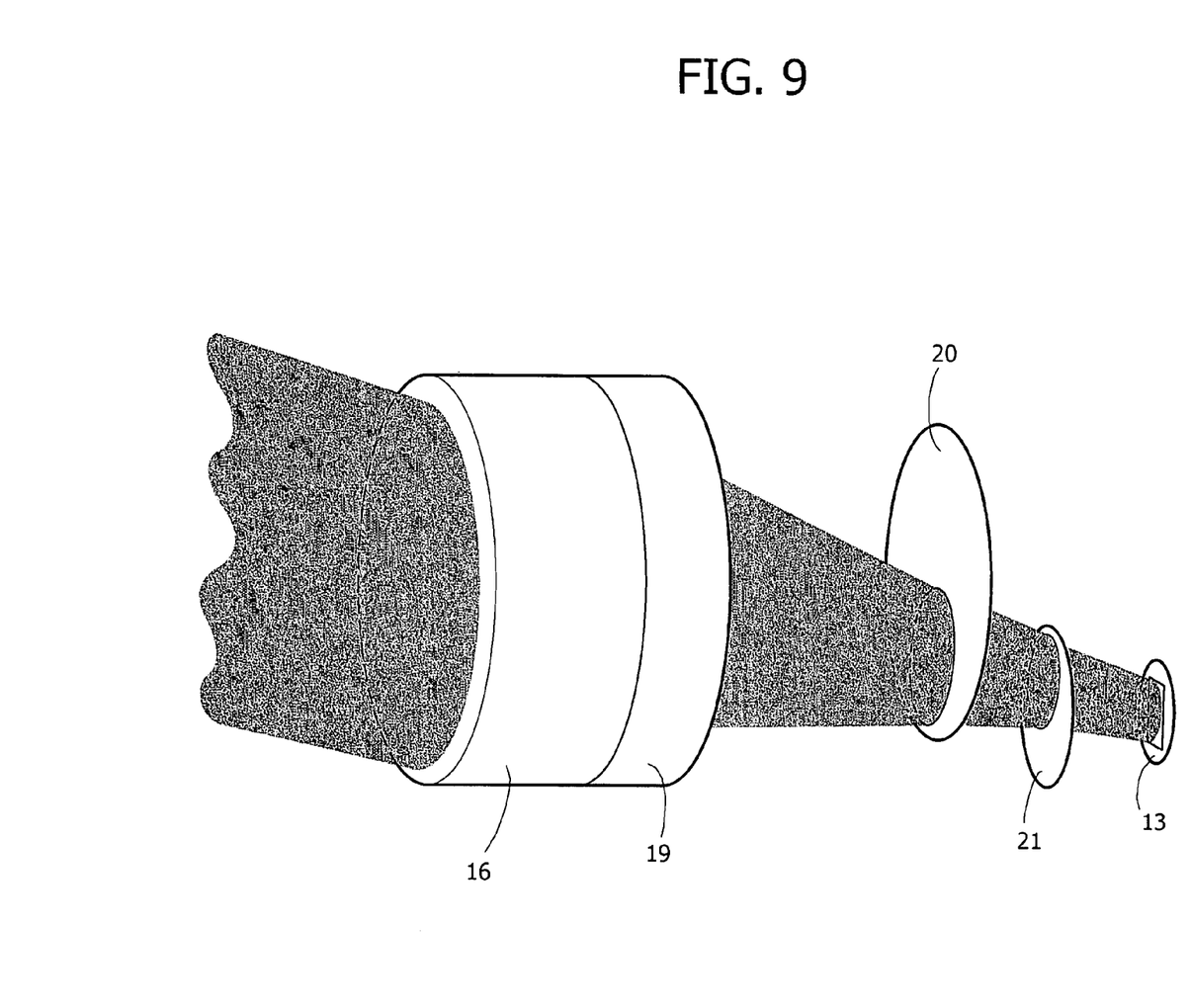
FIG. 9 is a schematic perspective view of the optical system indicated by the arrow IX in FIG. 5.

The LED 14 functioning as emitter for detection of fog is a LED in the near infrared. The lens 16 is preferably a plane-convex converging lens, associated to which is a bandpass filter 19 (see FIG. 9). As may be seen, the lens 16 is oriented with its optical axis not orthogonal to the windscreen W (FIG. 6) in so far as this could give rise to problems on account of reflection by the window, which could be more intense than the atmospheric back-scattering signal. Consequently, an orientation of the optical axis of the lens 16 not orthogonal to the windscreen has been chosen (FIG. 6). Furthermore, the LED 14 and the lens 16 are oriented in such a way that the field of vision of the receiver is superimposed on the beam leaving the LED in a point located beyond the windscreen W (FIG. 6).

Once again with reference to FIG. 9, downstream of the optical filter 19 are provided in series two diaphragms 20, 21, which limit the aperture of the beam that reaches the array 13.

Returning to FIG. 11, in the case of the example illustrated, the sensitive area of the sensor array 13 has a second sub-area adjacent to the bottom left vertex of the sensitive area, dedicated to detection of a twilight condition. Onto said sub-area are conveyed light signals coming from an optical system including an optical fibre (FIG. 5) having one end 22*a* oriented upwards and to the right with respect to the direction of travel of the vehicle. Said orientation derives from a compromise between the need to orient the sensor upwards, the constraints of space deriving from the presence of the other optical systems and the need to contain as much as possible the overall dimensions of the sensor.

Figure 10:
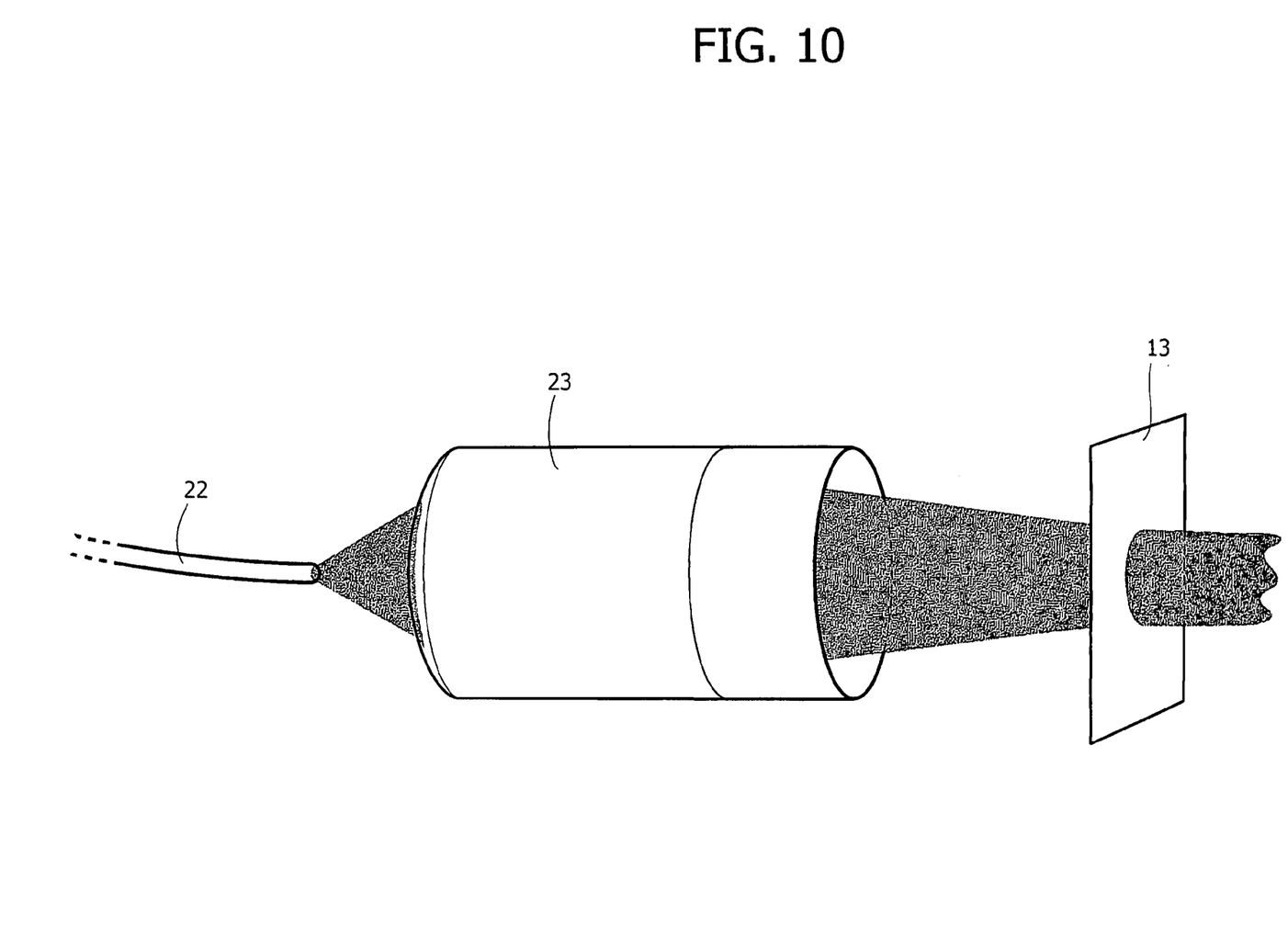
FIG. 10 is a schematic view of the optical system indicated by the arrow X in FIG. 5.

The rear end 22b of the optical fibre emits a divergent cone-shaped beam that is made to converge on the array 13 via a biconvex lens 23 (see also FIG. 10).

Figure 7:
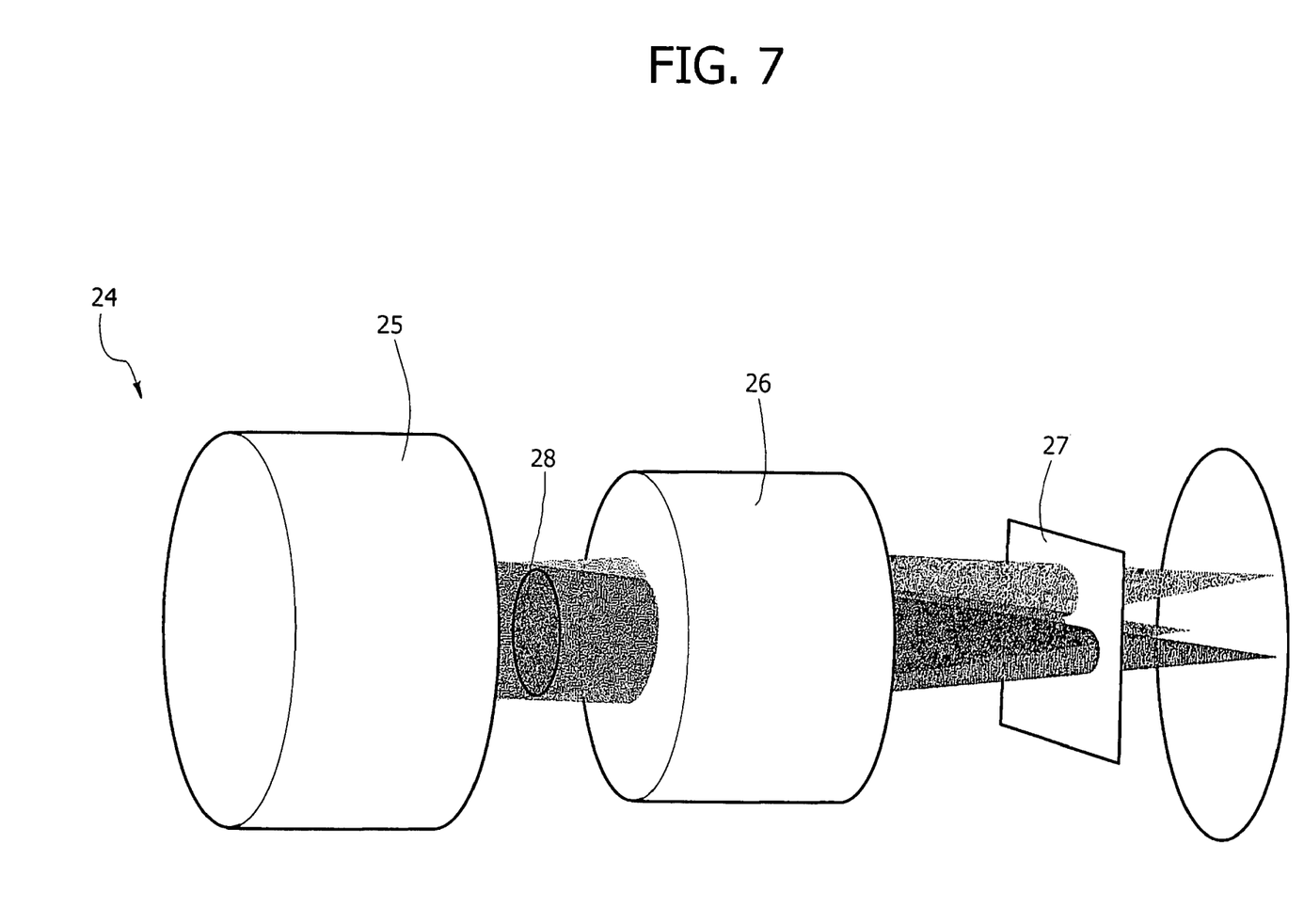
FIG. 7 is a schematic perspective view of the optical system indicated by the arrow VII in FIG. 5.

Again with reference to FIG. 11, the sensitive area of the array 13, in the case of the example illustrated, has a third sub-area adjacent to the bottom right vertex of the sensitive area (as viewed in FIG. 11) dedicated to monitoring the scene in front of the vehicle, with particular reference to detection of crossing another vehicle that is travelling in the opposite direction, and to detection of fog via the passive technique (i.e., exploiting only the radiation emitted by the scene and not the diffusion of light emitted by an emitter). Contained within said sub-area is a further sub-area dedicated to detecting a condition of passing through a tunnel. These functions are performed by means of an optical system 24, illustrated schematically and at an enlarged scale in FIG. 7, which directs the optical signals coming therefrom towards the aforesaid sub-area. The optical system 24 comprises a pair of lenses 25, 26, set one downstream of the other having an optical axis oriented in the direction of travel of the vehicle. The optical isolation of said function has been obtained with a rectangular field stop 27 of dimensions close to those of the image plane. Set between the two lenses 25 and 26 is a diaphragm 28; to be more precise, the diaphragm 28 is set in the area in which the beams leaving the lens 25 coming from different angles intersect, and, in practice, it is obtained by making a small circular opening 290 (FIG. 5) in the support 17. Also the field stop is preferably constituted by a rectangular opening made in the rear part of the support 17.

Figure 8:
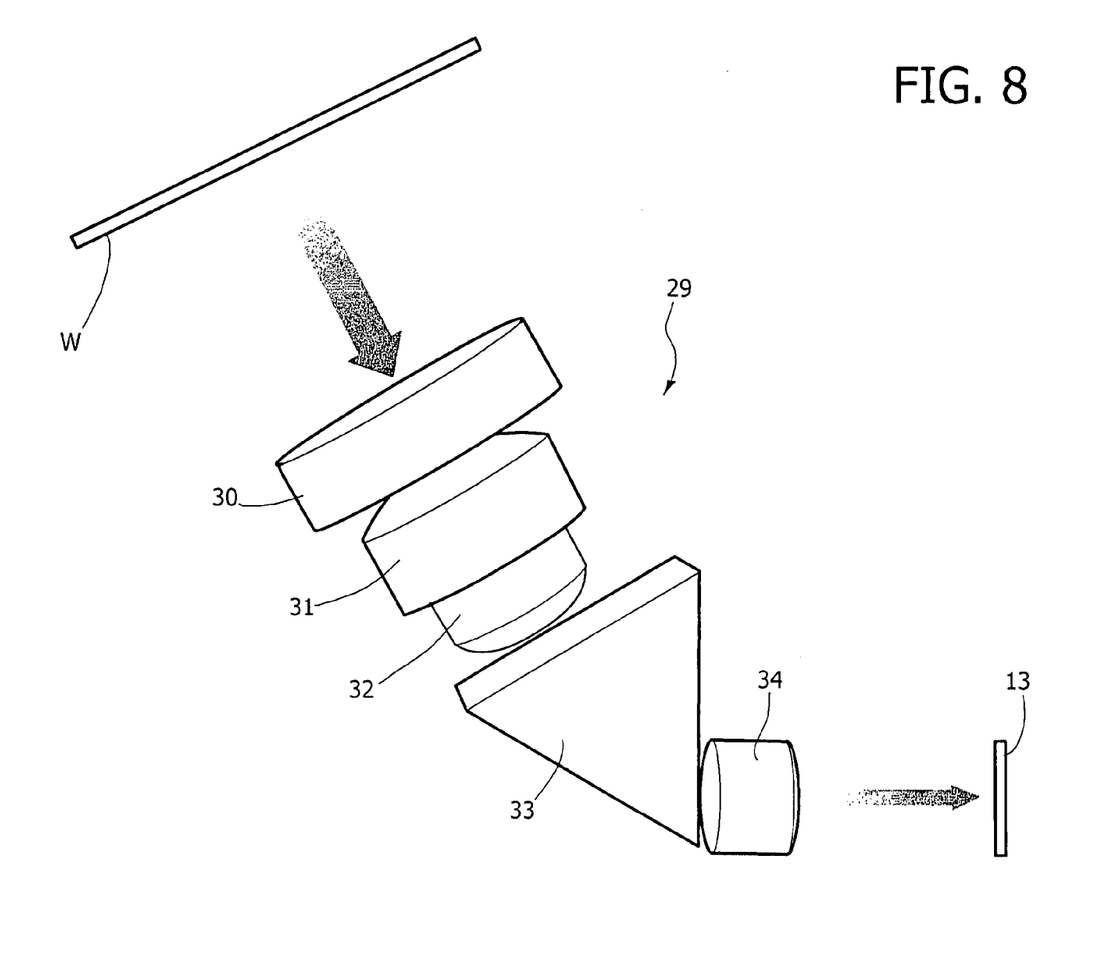
FIG. 8 is a schematic view of the optical system indicated by the arrow VIII in FIG. 5.

Once again with reference to FIG. 11, the sensitive area of the array 13 has, finally, a sub-area adjacent to the top left vertex (as viewed in FIG. 11) dedicated to detection of the presence of raindrops or mist on the windscreen, with the use of an active technique, i.e., exploiting the reflection of the light radiation coming from emitters that are provided in the cavity 3 of the support 2 (FIGS. 1, 3, 4). The light radiation emitted by the aforesaid emitters and reflected by raindrops or mist on the windscreen is received by an optical system 29 (FIG. 5), which is illustrated at an enlarged scale in FIG. 8. The optical system 29 comprises a NIR optical filter 30, a first lens 31, a second lens 32, a prism 33 and a third lens 34 set one downstream of the other. The optical system 29 focuses a portion of windscreen W. For this reason, the optical axis of the end of the system facing the windscreen is orthogonal to the windscreen, whilst the optical axis of the end of the system facing the sensor 13 is orthogonal to the sensor array. The deviation (for example, in the region of 60°) is obtained with the prism 33 operating in total reflection, or alternatively with a mirror. In the case of total reflection, the reflectance is maximum for both of the states of polarization with respect to the plane of incidence, whilst, as regards the solution with a metal mirror, the reflectance at 60° from the normal is not maximum (approximately 0.9 for aluminium) and is smaller in a polarization parallel to the plane of incidence (0.86) than that in an orthogonal polarization (0.95). The optical system 29 sets the main geometrical constraints for the device. The distance from the windscreen and the condition of wiping of the surface monitored determine, in fact, the position of the sensor device 1 in the vehicle. For the rain function, a system constituted by a LED in the near infrared and a plane-convex beam-shaping lens illuminates all the area concerned. For the misting function, a single narrow-divergence infrared LED produces a spot of radiation that is sufficiently small to discriminate certainly the presence of mist on the image plane and thus distinguish misting on the inside of the windscreen from misting on the outside. Both of the illuminators (not illustrated) are integrated in the cavity 3 of the support 2 and are aimed at the monitored area of the windscreen.

As may be seen in FIG. 5, the optical system 24 for front monitoring and the optical system 16 for detection of fog, the rear lens 34 of the optical system for detection of rain, and the lens 23 for focusing of the optical fibre for detection of the twilight condition are integrated in the support 17, which is, for example, made of anodized metal material. The remaining optics are inserted in an auxiliary support 35, which is also provided with fixing holes 35a for being fitted to the support 17, the frame 18 and the plate 11. The support 35 includes a casing 35b for the optical system 29. Spacers are provided to be applied between the plate 11 and the support 17 to obtain focusing, regardless of the tolerances of fabrication of the sensor 13.

According to a variant, the optical system 24 for detection of crossing of an oncoming vehicle can be constituted by an optical microzoom in order to increase the number of functions of front monitoring that can be performed with one and the same optics. In this way, it is possible to perform in sequence (sequential operation) functions characterized by their own specific fields of vision and range.

The sensor 13 can be of a CCD or CMOS type, with different resolution according to the number and type of integrated functions, whether monochromatic or colour. The sensor array can possibly integrate pre-processing functions at the pixel or chip level.

According to a preferred characteristic, the CMOS sensor has a logarithmic response so as to present a quasi-linear curve of the visibility (expressed in metres) as a function of the light intensity of the pixel and hence a greater resolution for levels of visibility higher than 100 metres.

According to a further preferred characteristic, the colour CMOS sensor is able to improve the robustness of the algorithm of estimation of the visibility. The RGB levels in the case of fog go into saturation, rendering the image less bright and tending to white.

The multifunctional sensor according to the invention can be used in different automotive applications, such as cars, lorries, buses, trams, agricultural machinery, earth-moving means with different configurations and combinations of functions.

If the device is integrated, as in the case of the example illustrated above, in the proximity of the windscreen, the functions performed can comprise, in addition to those already described above, functions such as detecting levelling of the vehicle, lane detection (for control of adaptive headlights or for functions of alarm for lane change), night vision, NIR scene detection, detection of road signs, detection of pedestrians, and "black box" functions.

The device can be integrated also in the proximity of the rear window of the motor vehicle. In this case, the useful functions are: detection of twilight, detection of rain/misting (internal and external) and ice on the window, detection of visibility (fog), and rear monitoring (for example as an aid to parking) Further functions that may be integrated in addition or as an alternative to the parking function are: monitoring of blind angle, monitoring vehicle levelling, lane detection (alarm for lane change), and black-box functions.

The device according to the invention can also be integrated in the external rear-view mirrors of the motor vehicle. In this case, the useful functions are: detection of twilight, detection of visibility, rear monitoring, and elimination of the blind angle of the rear-view mirror. Further functions that may be integrated are: aid to parking, detection of levelling, lane detection (alarm for lane change), and black box. In order to eliminate the blind angle of the rear-view mirror two different changes of view can be provided for covering different directions and ranges.

The functions to which the sensor device according to the invention is dedicated of course enables providing an aid to driving for the driver or automatically activating on-board devices.

For example, detection of a twilight condition, or detection of passing through a tunnel, can be used for automatic activation of switching-on and switching-off of the lights of the motor vehicle.

Detection of fog can be exploited for automatic activation of switching-on of front foglights and rear foglights, or the adjustment of the intensity of rear lights.

Detection of rain can be exploited for automatic activation or automatic deactivation of the windscreen-wiper device and for regulating the speed of the windscreen-wiper device.

Detection of crossing an oncoming vehicle can be exploited for controlling accordingly the driving beam of the motor vehicle.

Detection of the lane of travel can be exploited for generating alarms for undesirable lane change or for orienting the headlights on a bend.

Detection of the condition of levelling of the motor vehicle can be exploited for automatically regulating the orientation of the headlights in the vertical plane.

The sensor device according to the invention enables recording of the signals received in a memory, with the consequent possibility of downloading, following upon an accident, the images that might be useful also for determination of responsibility or for detecting the number-plates of other vehicles.

Finally, wireless communication is envisaged for transmitting data, for example, to an identifier device used on the vehicle also for other functions, such as storing vehicle data, personalizing the vehicle, and enabling opening of the doors and starting of the engine.

Of course, without prejudice to the principle of the invention, the details of construction and the embodiments may vary widely with respect to what is described and illustrated herein, without thereby departing from the scope of the present invention.

What is claimed is:

1. An optical sensor device of the type comprising:
   an optical sensor in the form of CCD or CMOS array, having a sensitive area in which a number of sub-areas is defined, each designed for a specific optical function corresponding to monitoring of the scene in front of a motor vehicle and/or to detection of environmental parameters; and
   a plurality of optical systems with different directions of the optical axis and/or fields of vision, designed to send optical signals to respective sub-areas of the sensitive area of said array in order to perform the aforesaid functions,
   in which at least some of said sub-areas are defined by different and separate portions of the sensitive area of said array dedicated to different optical functions, and
   in which said different and separate portions of the sensitive area of the array include at least:
   a first portion of the top part of the sensitive area, defining a first sub-area for detection of fog in front of the motor vehicle;
   a second and different portion of the sensitive area, defining a second sub-area, for detection of a twilight condition;
   a bottom portion of the sensitive area, defining a third sub-area, separated from said first sub-area and from said second sub-area, for monitoring the scene in front of the motor vehicle;
   a further portion of the top part of the sensitive area, defining a fourth sub-area different and separate from the first, second and third sub-areas, for detecting the presence of raindrops or mist on the windscreen or on the rear window of the motor vehicle; wherein the plurality of optical systems comprises
   a first optical system for conveying optical signals on said first sub-area for detection of fog, including a first light emitter for emitting light in the direction of the space in front of the motor vehicle, a receiver for receiving light scattered by the fog possibly present in front of the motor vehicle, and optical means for directing the light received only on said first sub-area of the sensitive area of said array; and
   a second optical system, a third optical system and a fourth optical system provided for directing optical signals on said second, third and fourth sub-areas of the sensitive area of said array, respectively for detection of a twilight condition, for monitoring the scene in front of the motor vehicle, with particular reference to a condition in which the vehicle crosses another vehicle coming in the opposite direction or to a condition of passing through a tunnel, and for detection of raindrops or of mist on the window of the motor vehicle,
   said optical sensor device being characterized in that:
   said first, second, third and fourth sub-areas of the sensitive area of the array occupy portions that are separate and at a distance from one another of the sensitive area of the array, adjacent, respectively, to four different vertices of the sensitive area of the array;
   said array is supported by a plate forming part of a sensor module incorporating at least part of the aforesaid optical systems;
   said sensor module is mounted within a supporting structure;
   said supporting structure supports the first emitter dedicated to the function of detecting fog, and a second emitter dedicated to the function of detecting rain and/or mist on the window of the motor vehicle;
   the first optical system is oriented according to an axis directed upwards and towards a side of the motor vehicle, not orthogonal to the windscreen, according to a cone that crosses the cone of lighting of first emitter in an area located beyond the windscreen;
   the third optical system comprises at least one lens having an optical axis parallel to the direction of travel;
   the second optical system comprises an optical fibre with a front end oriented upwards and on a side with respect to the direction of travel of the vehicle, and a rear end, associated to which is a lens for causing the outcoming light beam to converge on the respective sub-area of the array; and
   the fourth optical system comprises, at one end, a first lens facing the window of the motor vehicle, having its optical axis perpendicular to the window, and, at the other end, a second lens having its optical axis orthogonal to the array, and optical means set between said lenses for deflecting the beam coming from the first lens towards the second lens, the aforesaid optical components being mounted within a support fixed on said rear plate bearing the array that constitutes therewith the aforesaid sensor module.

2. The sensor device according to claim 1, wherein, downstream of the first optical system optical means, an optical filter and one or more diaphragms are provided.

3. The sensor device according to claim 1, wherein, downstream of the third optical system at least one lens, are set a further lens and a diaphragm for limiting the cross section of the beam coming from the optical system that is directed towards the respective sub-area of the array, a further diaphragm being set between the two lenses.

4. The sensor device according to claim 1, wherein the second optical system is a biconvex lens.

5. The sensor device according to claim 1, wherein the first and second emitter devices are LED sources in the near infrared.

6. The sensor device according to claim 1, wherein the supporting structure of the sensor module comprises two separate supporting plates, screwed together and to the rear plate bearing the sensor array, a first of said supporting plates carrying the third optical system at least one lens, the fourth optical system second lens, and the second optical system lens, the second supporting plate carrying the remaining optical components and incorporating, a casing for the fourth optical system, which comprises, in addition to the first lens, two further lenses set in series downstream of the first lens, and a total-internal-reflection prism that deflects the beam coming from said further lenses towards the second lens at the end of the system facing the array of the sensor.

7. The sensor device according to claim 6, wherein set between the rear plate bearing the array and the aforesaid supporting plates are spacers selected for focusing of the system.

8. The sensor device according to claim 1, wherein the third optical system comprises an optical microzoom.

9. The sensor device according to claim 1, wherein the array is of the CMOS type with logarithmic response.

10. The sensor device according to claim 1, wherein the array is of the colour-CMOS type.

11. The sensor device according to claim 1, wherein the sensor device is associated to an electronic control unit designed to activate automatically one or more on-board systems of the motor vehicle as a function of the signals received from said sensor device.

* * * * *